United States Patent [19]

Akin et al.

[11] Patent Number: 5,021,457

[45] Date of Patent: Jun. 4, 1991

[54] METHOD FOR AIDING CESSATION OF SMOKING

[75] Inventors: Frank J. Akin; Robert Klesges; Lisa Klesges, all of Germantown, Tenn.

[73] Assignee: Plough Inc., Memphis, Tenn.

[21] Appl. No.: 391,814

[22] Filed: Aug. 9, 1989

[51] Int. Cl.⁵ .............................................. H01N 33/02
[52] U.S. Cl. .................................... 514/653; 514/813
[58] Field of Search ................................. 514/813, 653

Primary Examiner—Stanley J. Friedman
Assistant Examiner—Greg Hook
Attorney, Agent, or Firm—John Maitner; Stephen I. Miller; James Nelson

[57] ABSTRACT

Individuals are aided in smoking cessation by administering internally phenylpropanolamine.

7 Claims, No Drawings

METHOD FOR AIDING CESSATION OF SMOKING

BACKGROUND OF THE INVENTION

The health consequences and medical costs associated with cigarette smoking are extremely well established. There are now more than 50,000 studies linking cigarette smoking to increased morbidity and mortality from cardiovascular diseases, various forms of cancer, and chronic obstructive lung diseases. It is estimated that annually in the United States, smoking is causually related to 170,000 deaths from cardiovascular disease, 130,000 deaths from cancer, and 50,000 deaths from chronic obstructive lung disease. As many as one third of heavy smokers who are now 35 years old will die before age 85 of diseases caused by their smoking. The estimated cost of health problems associated with smoking, including medical care, absenteeism, decreased work productivity, and accidents is estimated to be $56 billion per year.

Given the consistent demonstration of dose-dependent relationships between smoking and disease, evidence of reductions in health risks following smoking cessation, and experimental studies documenting carcinogenic effects of tobacco smoke in animals, few scientists question the causal nature of the relationship between smoking and illness. Despite this, approximately 26% of the adults in the United States continue to smoke. Very few effective strategies for smoking cessation have been developed, and up to 80% of smokers who initially stop smoking will relapse within six months to a year. The potential success of smoking cessation efforts is impeded, in part, by the fact that many of the advantages of continuing to smoke are immediate while the disadvantages of smoking are delayed and probabilistic.

One immediate consequence of quitting smoking is weight gain. There is overwhelming evidence that smoking cessation leads to weight gain. The 1988 *Surgeon General's Report* (USPHS, 1988) reported on the results of 28 cross-sectional evaluations of smoking and body weight as well as 43 studies that evaluated smoking and body weight status over time. Of the 71 studies evaluated, 62 (87%) collectively indicated that smokers weigh less than nonsmokers and that people who quit smoking gain weight. For the cross-sectional studies, it was reported that smokers weighed an average of 7.13 lb (range: 2.36–14.99 lb) more than nonsmokers. Smokers who quit in the longitudinal studies gained an average of 6.16 lb (range: 1.76–18.07 lb) following cessation. A popular, but erroneous, statistic is that only about one third of smokers will gain weight following cessation, while one third stay the same weight and one third lose weight. Unfortunately, recent studies have confirmed that the overwhelming majority of smokers gain weight following cessation.

Unfortunately, weight gain following smoking cessation appears to be a significant reason for continued smoking. At least one third of smokers report that they continue to smoke primarily for the weight-related benefits. It also appears that some individuals, particularly females, are likely to initiate smoking because of the weight reduction properties of cigarettes. Weight-related concerns also appear to be an important predictor of success in both worksite and pharmacologic intervention.

Although weight and weight-related concerns appear to be a major reason for continued smoking, it may be surprising to learn that there are few effective treatment methods for reducing this inevitable weight gain. Behavioral methods, which are effective in weight control in general, have not yet been developed to the extent where they can prevent, or even reduce, postcessation weight gain. In terms of pharmacologic-intervention, some investigators have advocated the use of nicotine chewing gum to aid in reducing postcessation weight gain. Reports of its effectiveness are variable, with nicotine chewing gum being clearly effective only if (a) the individual is a heavy smoker and (b) the individual uses large amounts of nicotine chewing gum. Also, a significant percentage of those using nicotine gum will continue to do so up to one year after smoking cessation. As such, its use as an aid to primarily reduce postcessation weight gain has been questioned.

Given these findings, there is a need to test both pharmacologic and non-pharmacologic methods to reduce postcessation weight gain. A promising drug product for this purpose is phenylpropanolamine (ppa). In addition to its appetite suppressant effects, phenylpropanolamine has been shown to increase metabolic rate in laboratory animals. The observation of increased metabolic rate is an important contribution given the strong evidence that smokers have elevated metabolic rates relative to nonsmokers.

U.S. Pat. No. 4,255,439 discloses a means and method for aiding individuals to stop tobacco smoking and lose overweight by administering a combination of an imidazoline derivative with an anorectic. The preferred imidazoline derivative is 2-(2,6-dichlorophenylamine)-2-imidazoline hydrochloride (clonidine hydrochloride), and the preferred anorectic is phentermine resin. Phenylpropanolamine is mentioned as an anorectic that can be used in place of the phentermine resin.

U.S. Pat. No. 4,639,368 discloses a chewing gum composition for supplying a medicament orally, which medicament is capable of being absorbed through the buccal cavity. The composition comprises a medicament, for example phenylpropanolamine and a carbon dioxide generator. Phenylpropanolamine is disclosed as an example of a medicament which is utilized as an anorectic or as a decongestant.

SUMMARY OF THE INVENTION

It is an object of this invention to provide a method for aiding individuals on smoking cessation by administration of phenylpropanolamine.

According to the invention a method of aiding individuals to stop smoking comprises administering phenylpropanolamine for oral ingestion over a time span of a few weeks.

DETAILED DESCRIPTION OF THE INVENTION

The following method was utilized to determine the effects of ppa on smoking cessation as well as its effects on weight gain in subjects at risk for weight increase following smoking cessation.

METHOD

Subjects

Subjects were adult female cigarette smokers who had reported experiencing weight gain following previous cessation attempts. To qualify for the study, subjects must have reported smoking at least 10 cigarettes a day continuously for the previous year. Levels of carbon monoxide in expired breath (a biochemical index of smoking status) had to exceed 15 ppm. Subjects were excluded if they had a history of cardiovascular disease, if they were taking any products containing phenylpropanolamine, if they were pregnant, if they were currently using a weight reduction aid, or if they had any condition that would affect dietary intake. Subjects receiving gum agreed to chew only the gum provided during the cessation trial.

Characteristic of Resultant Sample

Of the 57 subjects attending the first meeting, 41 (72%) were successful at quitting smoking throughout the 2-week period. Successful abstainers averaged 28.02 years of age (SD=7.56) and reported, at baseline, that they consumed an average of 22.5 cigarettes per day SD=10.16, Range 10-50 cigarettes). Participants indicated that they had been smoking for an average of 12.98 years (SD=11.46). Subjects indicated that in the past they had tried to quit smoking an average of 5.7 times (SD=12.92) and had reported an average weight gain of 6.53 lb SD=9.9, Range=−10 to +45 lb) in previous quit attempts. There were no significant between groups differences at baselines on any of these variables.

At baseline assessment, subjects weighed an average of 136.15 lb. (SD=24.11) and subjects averaged 63.27 inches (SD=3.22). Carbon monoxide levels in expired breath averaged 48.49 parts-per-million (SD=32.35, Range=15-179). This mean carbon monoxide level indicates that our subjects were very heavy smokers. There were no significant between groups differences at baseline on height or weight. A correlation between baseline carbon monoxide levels and relative weight indicated a significant linear relationship ($r=-0.44$, $o=0.005$). As carbon monoxide levels increased, relative body weight decreased.

Procedure

After an initial screening, subjects came to the laboratory once a week for four weeks. During the first baseline assessment, subjects completed a medical history. Resting blood pressure was taking using an automated blood pressure system and utilizing a standardized protocol (i.e., 4 blood pressures taken a minute apart, the first reading was discarded, and the next three readings were averaged). A complete smoking an dieting history was then obtained on each subject. To confirm current smoking status, carbon monoxide assessments were also collected; height and weight measurements were taking privately. Finally, levels of weekly dietary intake were acquired through a semiquantitative 1-week food frequency questionnaire as were levels of weekly physical activity.

A brief, but intensive stop-smoking intervention was given to all participants.

Subjects were randomly assigned to one of three treatment conditions in a double-blind procedure. In the phenylpropanolamine gum group, subjects were given a week's supply of 8.33 mg phenylpropanolamine gum (Stay Trim, Schering-Plough, Inc., Memphis, Tenn) in individual blister packages. Subjects were instructed to chew the gum according to the manufacturer's recommendations; that is, chew three 8.33 mg pieces three times a day before meals. In the placebo gum group, subjects were given an identical gum in shape, color, size, and taste except that the active ingredient (phenylpropanolamine) was removed. In the no gum group, subjects were told to quit smoking and were not given a gum product. Neither the investigators nor the subjects knew which gum contained the active ingredient. The on site supervisor had two boxes of gum (marked "A" and "B"); he in turn gave gum without comment to research assistants who were responsible for data collection. This procedure eliminated any guesswork by the research assistants regarding observed trends in the data. The investigator became aware of which gum contained ppa only after all analyses were completed.

Initially, all subjects were randomly assigned to treatment conditions. However, as the trial progressed, it was apparent that differential drop out rates were observed in two of three conditions (see Results section). Thus, a stratified random sampling procedure was employed, whereby subjects were still randomly assigned to conditions, but oversampling was conducted in two of the three conditions.

After completing the assessment and treatment protocol, subjects were told that they must stop smoking for a period of 14 days. All subjects had to agree not only to biochemical verification of smoking status (via carbon monoxide testing) but also submit to a random carbon monoxide abstinence verification check. Given the short half-life of carbon monoxide, it is conceivable that subjects could quit smoking for the 24 hours prior to their weekly laboratory assessments and achieve a carbon monoxide level within the nonsmoking range. To prevent this possibility, subjects were told that they were to participate in random (spot) carbon monoxide checks. That is, without notice on either a weekday or weekend, a research assistant would contact the participant and take an on-the-spot carbon monoxide reading. Anyone not achieving a normal carbon monoxide reading, or anyone later refusing a carbon monoxide spot check, was classified as a smoker and eliminated from the data analysis.

Subjects returned to the laboratory 7 days and then again 14 days later. Assuming they were still abstinent (any subjects reporting smoking or failing their carbon monoxide assessment [i.e., $COs \geq 10$ ppm] were dismissed from the study), blood pressure, carbon monoxide, height, weight, dietary intake, and physical activity patterns information were again obtained.

Following the third week, subjects were told that they could resume smoking if they wished, although they were encouraged to maintain abstinence. Subjects were seen a fourth week (a follow-up, or return to baseline week), in which height, weight, and carbon monoxide assessments were obtained.

RESULTS

The Effects of Intervention on Smoking Cessation

As indicated above, 41 of 57 (72%) subjects were successful in continuously abstaining from smoking for the 2-week period. However, differential cessation rates were observed by condition, as illustrated in Table 1.

TABLE 1

| | Cessation Rates by Condition | | | |
|---|---|---|---|---|
| Condition | Quit (n) | Not Quit (n) | Total (n) | Percent |
| PPA Gum | 15 | 1 | 16 | 94%* |
| Placebo Gum | 12 | 9 | 21 | 57% |
| No Gum | 14 | 6 | 20 | 70% |
| Total | 41 | 16 | 57 | 72% |

*Denotes a significant between groups difference ($X = [2] = 6.08$, $p < .05$).

Among those subjects receiving ppa gum, 15 of 16 (94%) subjects were successful in quitting smoking. In contrast, only 12 of 21 (57%) subjects in the placebo gum and 14 of 20 (70%) subjects in the no-gum conditions were successful ($X=[2]=6.08$, $p<0.05$). Relative to the other two groups, subjects receiving the ppa gum were more successful in quitting smoking ($X=[1]=5.25$, $p=0.022$).

In the treatment of this invention, phenylpropanolamine is preferably used in dosages which can vary depending upon the individual although doses of from 25 mgs to 75 mgs daily are possible. A dosage of 25 mgs three (3) times a day for several weeks was sufficient to obtain smoking cessation results.

As representative suitable oral dosage formulations which can be employed in the practice of this invention, the following are examples: tablets, e.g. immediate release and sustained release tablets; lozenges, chewing gums and the like. The preferred dosage form is a chewing gum.

The following are examples of oral dosage formulations of this invention following the method of this invention. The preparation of the various dosage form, e.g. tablets, lozenges and chewing gums, are prepared by conventional techniques well known to those skilled in the art.

EXAMPLE 1

| Compressed Lozenge | | |
|---|---|---|
| Ingredient | Percent | mg/tab |
| PART A | | |
| Sorbitol Tablet Type | 15.00000 | 198.750 |
| Saccharin, Sodium Powder FCC | 00.12000 | 1.590 |
| Phenylpropanolamine Hydrochloride USP | 00.99057 | 13.125 |
| Color | 00.04000 | 0.530 |
| PART B | | |
| Sorbitol Tablet Type | 82.39943 | 1091.792 |
| Flavor | 00.75000 | 9.938 |
| PART C | | |
| Magnesium Stearate, NF | 00.70000 | 9.275 |
| TOTAL | 100.00000 | 1325.000 |

EXAMPLE 2

| Sustained Release (12 hr.) Tablet | | |
|---|---|---|
| Component | % w/w | mg/tablet |
| Phenylpropanolamine HCl | 16.67 | 75 |
| Lactose | 60.67 | 273 |
| Hydroxypropyl Methylcellulose (USP 2910) | 222.22 | 100 |
| Magnesium Stearate | 0.44 | 2 |
| TOTAL | 100 | 450 |

EXAMPLE 3

| Immediate Release Tablet | | |
|---|---|---|
| Component | % w/w | mg/tablet |
| Phenylpropanolamine HCl | 8.3% | 25 mg |
| Modified Cellulose Gum (Ac-Di-Sol) | 2.0% | 6 mg |
| Magnesium Stearate (NF) | 1.0% | 3 mg |
| Dicalcium Phosphate (NF) | 44.7% | 134 mg |
| Lactose (NF) (Fast Flo) | 44.0% | 132 mg |
| TOTAL | 100.0% | 300 mg |

EXAMPLE 4

| Gum | | |
|---|---|---|
| Ingredient Description | Quantity | % w/w |
| PART A | | |
| Water Purified USP | 12.00 | 1.50 |
| Phenylpropanolamine | 7.33 Kg | 0.92 |
| PART B | | |
| Gum Base | 232.00 Kg | 29.00 |
| Sugar, Standard Granulated | 165.21 Kg | 20.65 |
| PART C | | |
| Water Purified USP | 4.00 Kg | 0.50 |
| PART D | | |
| Sugar, Standard Granulated | 165.99 Kg | 20.75 |
| Glucose, Spray Dried | 128.00 Kg | 16.00 |
| PART E | | |
| Sugar, Standard Granulated | 37.73 Kg | 4.72 |
| Flavor | 6.00 Kg | 0.75 |
| Sugar, Standard Granulated | 41.73 Kg | 5.22 |
| TOTAL | 800 Kg | 100% |
| PART F | | |
| Dusting Powder | 100.000 Kg | As needed |
| (Sugar) | (75.00 Kg) | |
| (Starch) | (25.00 Kg) | |

EXAMPLE 5

| Hard Candy Lozenge | | |
|---|---|---|
| Component | % wt/wt added | % wt/wt cooked |
| PART A | | |
| Sugar | 48.6951% | 58.92% |
| Corn Syrup | 40.0782% | 39.28% |
| Water | 9.7390% | — |
| PART B | | |
| Glycerin USP 99% | 0.8265% | 1.0000% |
| Phenylpropanolamine HCl | 0.4132% | 0.50000% |
| PART C | | |
| Color (as desired) | 0.0413% | 0.0500% |
| Flavor (as desired) | 0.2066% | 0.2500% |
| TOTAL | 100.0000% | 100.0000% |

EXAMPLE 6

| Dietetic Lozenge | | |
|---|---|---|
| Component | % wt/wt | % wt/wt |
| PART A | | |
| 70% Sorbitol Solution | 98.7331% | 98.2000% |
| PART B | | |
| Phenylpropanolamine HCl | 0.3519% | 0.5000% |
| Glycerin USP 99% | 0.7038% | 1.0000% |
| PART C | | |
| Color (as desired) | 0.0352% | 0.0500% |
| Flavor (as desired) | 0.1760% | 0.2500% |
| TOTAL | 100.0000% | 100.0000% |

We claim:

1. A method of aiding individuals in smoking cessation, said method comprising administering to an individual in need thereof an effective amount of phenylpropanolamine.

2. The method of claim 1 wherein the phenylpropanolamine is administered by an oral ingestion dosage form.

3. The method of claim 2 wherein the phenylpropanolamine is administered by oral ingestion at a dosage rate of from about 25 to about 75 mg a day.

4. The method of claim 3 wherein the phenylpropanolamine is administered by oral ingestion at a dosage rate of 75 mgs a day.

5. The method of claim 2 wherein the dosage form is a chewing gum.

6. The method of claim 2 wherein the dosage form is a lozenge.

7. The method of claim 2 wherein the dosage form is a tablet.

* * * * *